US007971491B2

(12) United States Patent
Greszczuk

(10) Patent No.: US 7,971,491 B2
(45) Date of Patent: Jul. 5, 2011

(54) APPARATUS AND METHOD FOR TRANSVERSE TENSILE STRENGTH TESTING OF MATERIALS AT EXTREME TEMPERATURES

(75) Inventor: Longin B. Greszczuk, Misslon Viejo, CA (US)

(73) Assignee: The Boeing Company, Chicago, IL (US)

( * ) Notice: Subject to any disclaimer, the term of this patent is extended or adjusted under 35 U.S.C. 154(b) by 184 days.

(21) Appl. No.: 12/400,287

(22) Filed: Mar. 9, 2009

(65) Prior Publication Data
US 2010/0224007 A1 Sep. 9, 2010

(51) Int. Cl.
G01N 3/08 (2006.01)

(52) U.S. Cl. ............................................ 73/826; 73/831
(58) Field of Classification Search .................... 73/826, 73/831, 856, 862
See application file for complete search history.

(56) References Cited

U.S. PATENT DOCUMENTS

| 5,431,062 | A | * | 7/1995 | Baratta | 73/856 |
| 5,528,942 | A | * | 6/1996 | Baratta | 73/856 |
| 6,079,277 | A | * | 6/2000 | Chung | 73/774 |
| 6,732,591 | B2 | * | 5/2004 | Miles et al. | 73/808 |
| 7,021,155 | B2 | * | 4/2006 | Imamura | 73/797 |
| 7,204,152 | B2 | * | 4/2007 | Woodward et al. | 73/794 |
| 7,204,153 | B2 | * | 4/2007 | Phipps | 73/808 |
| 7,392,717 | B1 | * | 7/2008 | Vacek | 73/862.631 |
| 7,798,014 | B2 | * | 9/2010 | Ferguson et al. | 73/831 |

OTHER PUBLICATIONS

Munjal, "Test Methods for Determining Design Allowables for Fiber Reinforced Composites," ASTM STP 1003, pp. 110, 1989.
"Standard Test Method for Through-Thickness "Flatwise" Tensile Strength and Elastic Modulus of a Fiber-Reinforced Polymer Matrix Composite Material," ASTM D7291/D7291M-07, 10 pages, 2007.
"Stresses in a Circular Disk," Theory of Elasticity, McGraw-Hill Book Co., pp. 122-126, 1970.

* cited by examiner

*Primary Examiner* — Freddie Kirkland, III
(74) *Attorney, Agent, or Firm* — Klintworth & Rozenblatt IP LLC

(57) ABSTRACT

A composite specimen for conducting transverse tension strength testing may include a solid cylinder comprising parallel opposing ends, a cylindrical surface extending between and around the parallel opposing ends, and only parallel planar plies extending between and perpendicular to the parallel opposing ends. The parallel planar plies may comprise fibers extending within the parallel planar plies.

33 Claims, 4 Drawing Sheets

APPARATUS AND METHOD FOR TRANSVERSE TENSILE STRENGTH TESTING OF MATERIALS AT EXTREME TEMPERATURES

FIELD OF THE INVENTION

The disclosure relates to apparatus and methods for measuring the transverse tension strength of a composite specimen.

BACKGROUND OF THE DISCLOSURE

It is often necessary to measure the transverse tension strength of composite specimens at various temperatures. Many of the conventional apparatus and methods utilize specimens that require grips for applying tension load to the specimen. For instance, one such conventional apparatus utilizes a dog-bone-shaped specimen having a narrower central portion and wider end portions which allow an appropriate device to grip the specimen. However, using a gripped specimen, and the machinery required for testing such a gripped specimen, may increase the time required for manufacturing the specimen, may increase the time required for conducting the testing, may increase cost, and/or may require complex testing equipment and methods of testing, especially at cryogenic and elevated temperatures. Other conventional apparatus and methods for measuring the transverse tension strength of a specimen may experience one or more additional types of problems.

An apparatus and method is needed which may solve one or more problems of one or more of the conventional apparatus and methods for measuring the transverse tension strength of a specimen.

SUMMARY OF THE DISCLOSURE

In one embodiment a composite specimen is provided for conducting transverse tension strength testing. The composite specimen may comprise a solid cylinder comprising parallel opposing ends, a cylindrical surface extending between and around the parallel opposing ends, and only parallel planar plies extending between and perpendicular to the parallel opposing ends. The parallel planar plies may comprise fibers extending within the parallel planar plies.

In another embodiment, a transverse tension strength measuring apparatus is disclosed. The transverse tension strength measuring apparatus may comprise a load-applying member, a support member, and a composite specimen. The load-applying member may be for applying a compression load. The support member may be disposed in alignment with the load-applying member. The composite specimen may comprise a solid cylinder comprising parallel opposing ends, a cylindrical surface extending between and around the parallel opposing ends, and only parallel planar plies extending between and perpendicular to the parallel opposing ends. The parallel planar plies may comprise fibers extending within the parallel planar plies. Opposite ends of the cylindrical surface of the composite specimen may be oriented between the support member and the load-applying member so that the load-applying member will apply the compression load to the cylindrical surface in a direction parallel to the parallel planar plies.

In yet another embodiment, a method is disclosed for measuring a transverse tension strength of a composite specimen. In one step, a composite specimen may be provided comprising a solid cylinder comprising parallel opposing ends, a cylindrical surface extending between and around the parallel opposing ends, and only parallel planar plies extending between and perpendicular to the parallel opposing ends. The parallel planar plies may comprise fibers extending within the parallel planar plies. In another step, opposite ends of the cylindrical surface of the composite specimen may be disposed between members of a transverse tension strength measuring apparatus. In still another step, a compression load may be applied to the cylindrical surface of the composite specimen in a direction parallel to the parallel planar plies using the members of the transverse tension strength measuring apparatus. In an additional step, a failure of the composite specimen may be detected due a transverse tensile stress in the composite specimen occurring transverse to the parallel planar plies. In still another step, the transverse tension strength of the composite specimen may be determined.

These and other features, aspects and advantages of the disclosure will become better understood with reference to the following drawings, description and claims.

DETAILED DESCRIPTION OF THE DISCLOSURE

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims.

Figure 1:
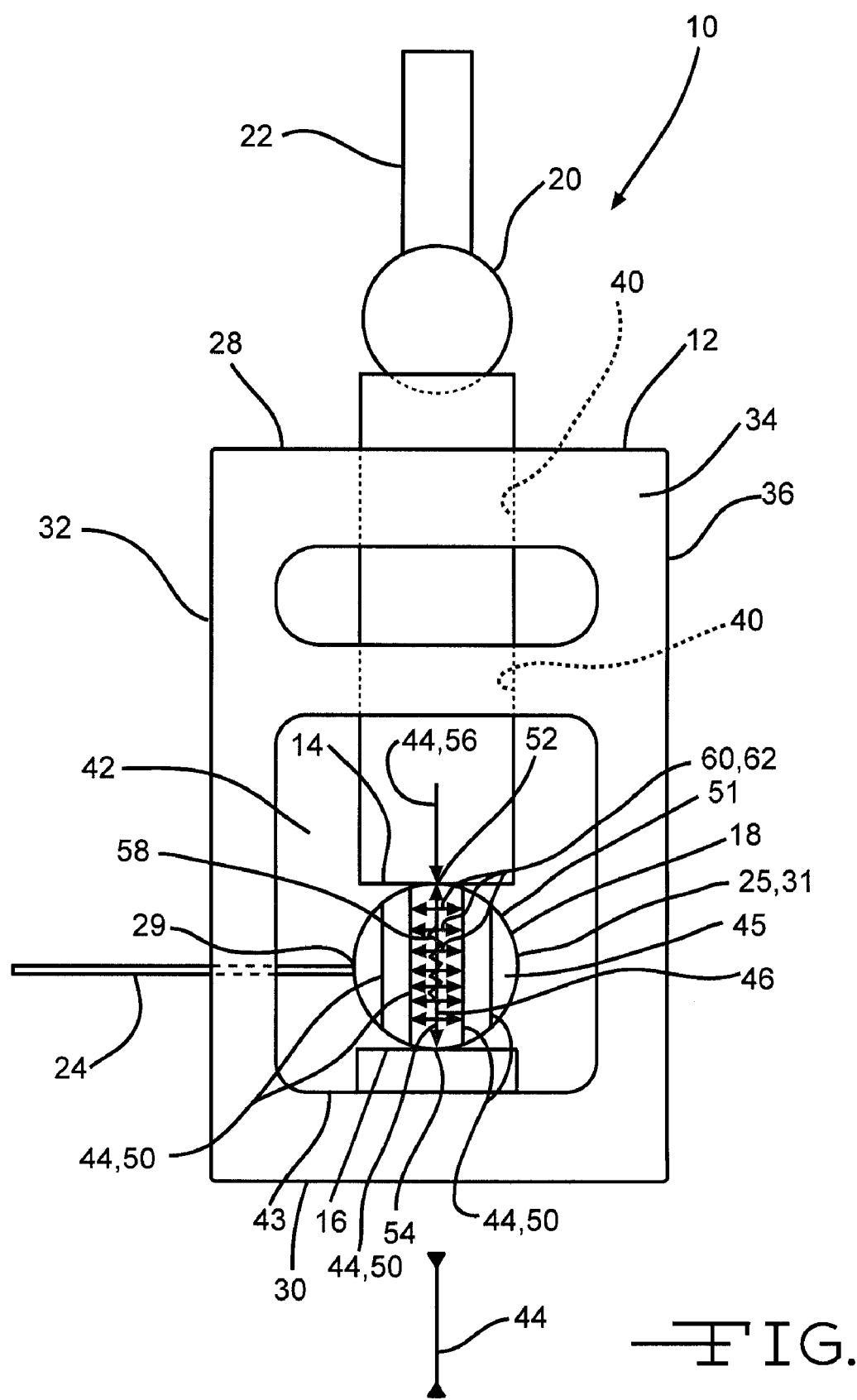
FIG. 1 illustrates a front view of one embodiment of a transverse tension strength measuring apparatus.
Figure 2:
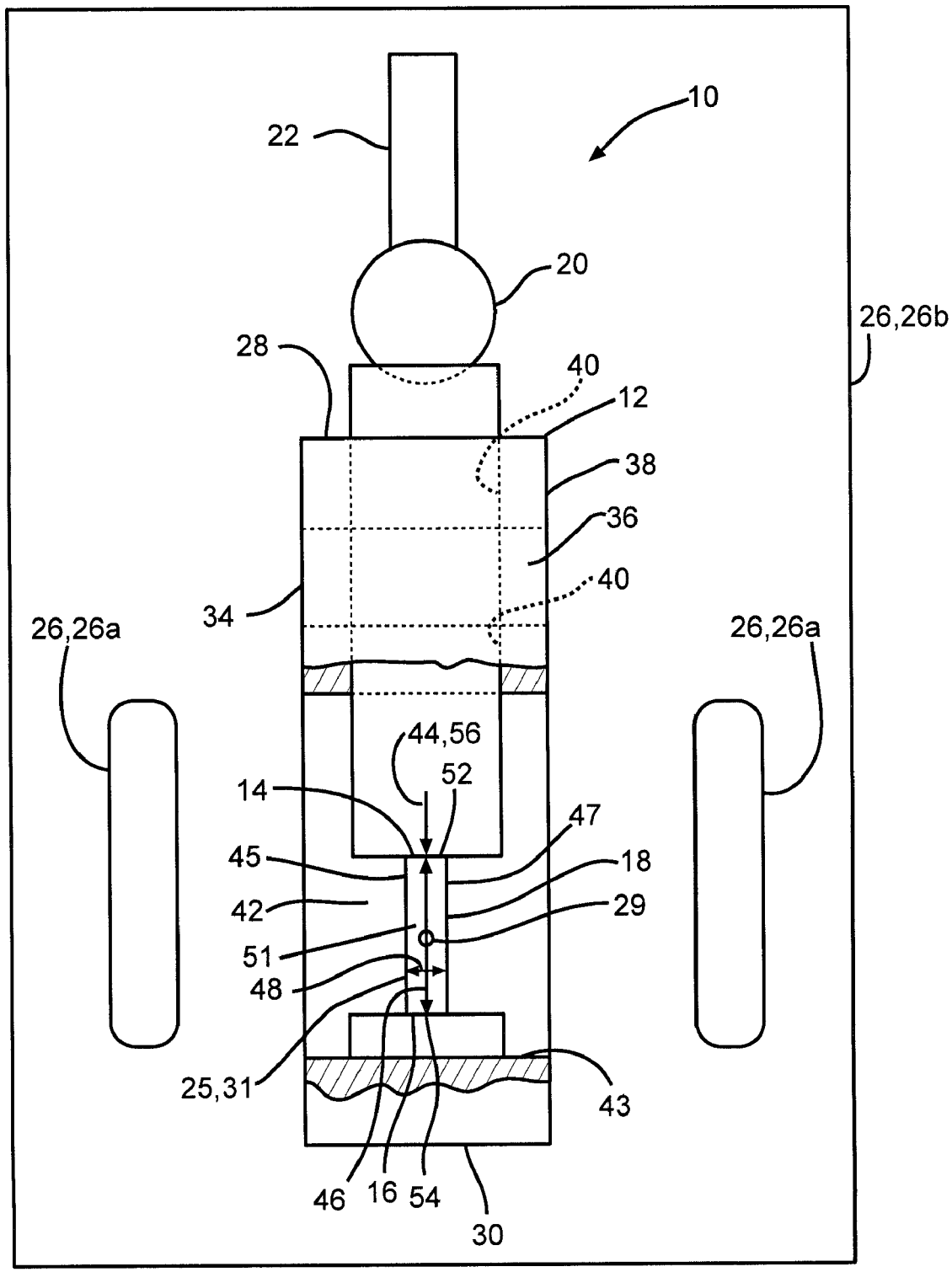
FIG. 2 illustrates a side, partial, cut-away view of the transverse tension strength measuring apparatus of FIG. 1.

FIGS. 1 and 2 illustrate front and side-partial-cut-away views of one embodiment of a transverse tension strength measuring apparatus 10. The apparatus 10 may comprise a housing 12, members 14 and 16, a composite specimen 18, a bearing 20, a test machine 22, a temperature-measuring device 24, and a temperature-changing device 26. In other embodiments, the apparatus 10, including any of its components, may vary. The housing 12 may have a top surface 28, a bottom surface 30, and side surfaces 32, 34, 36, and 38. The top surface 28 may be defined by a hole 40 extending from the top surface 28 towards the bottom surface 30. At least one side surface 34 may be defined by a cavity 42 extending from the side surface 34 towards another of the side surfaces 38. The hole 40 and the cavity 42 may intersect within the housing 12. Member 14 may comprise at least one of a load-applying member and a loading pin. Member 14 may be moveably disposed in the hole 40 in a direction 44. Member 16 may be disposed within the cavity 42 in alignment with member 14. Member 16 may comprise at least one of a support member and a stationary plate. Member 16 may be disposed against a bottom surface 43 of the cavity 42.

Figure 3:
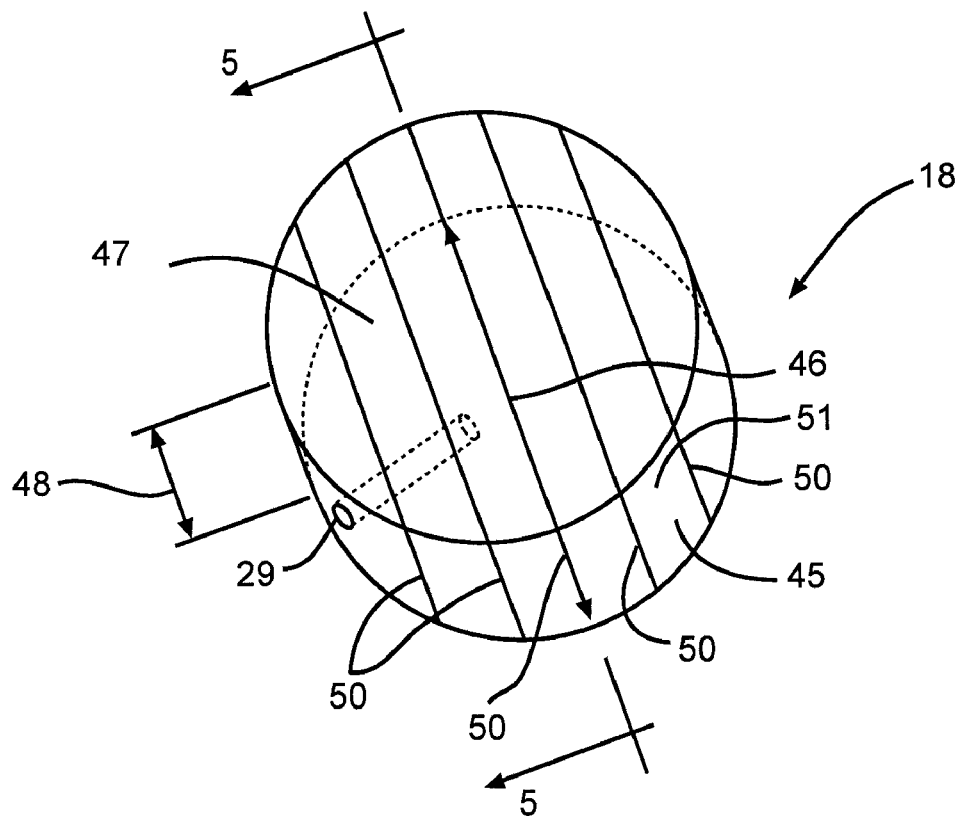
FIG. 3 illustrates a perspective view of one embodiment of a composite specimen which may be tested by the transverse tension strength measuring apparatus of the embodiment of FIGS. 1 and 2.
Figure 4:
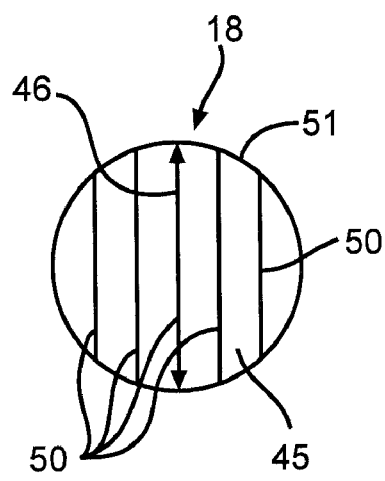
FIG. 4 illustrates a front view of the composite specimen of FIG. 3.
Figure 5:
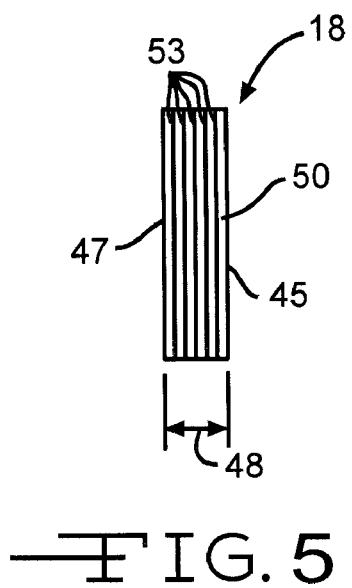
FIG. 5 illustrates a cross-sectional view through line 5-5 of the composite specimen of FIG. 3.

FIGS. 3, 4, and 5 illustrate perspective, front, and cross-sectional views (through line 5-5 of FIG. 3) of the composite specimen 18 of FIGS. 1 and 2. As shown in FIGS. 3-5, the composite specimen 18 may comprise a solid cylinder, which may comprise a disc or a short cylinder, having parallel opposing ends 45 and 47 and a cylindrical surface 51 extending between and around the parallel opposing ends 45 and 47. Only parallel planar plies 50 may extend between and perpendicular to the parallel opposing ends 45 and 47. In one embodiment, the parallel planar plies 50 may comprise only parallel fibers 53 extending within the parallel planar plies 50 parallel to the parallel opposing ends 45 and 47. In other embodiments, the parallel planar plies 50 may comprise fibers 53 extending in varying parallel and non-parallel orientations within the parallel planar plies 50. The composite specimen 18 may comprise a diameter 46 of the parallel opposing ends 45 and 47, and a thickness 48 comprising a distance between the parallel opposing ends 45 and 47. The thickness 48 may be substantially shorter than the diameter 46 so that the composite specimen 18 forms a disc or a short cylinder to allow a uniform temperature of the composite specimen 18. In one embodiment, the thickness 48 may comprise at least one-quarter of the diameter 46. It may be important that the composite specimen 18 comprise a thickness 48 which is not too much larger than one-quarter of the diameter 46 because it may be difficult to obtain a uniform temperature throughout the composite specimen 18 if the thickness 48 is too large. Conversely, it may be important that the thickness 48 is not too much smaller than one-quarter of the diameter 46 to prevent the composite specimen 18 from buckling upon application of a compressive load. In other embodiments, the thickness 48 and diameter 46 may vary. The cylindrical surface 51 may be defined by an aperture 29 for connecting to the temperature-measuring device 24 of FIGS. 1 and 2.

As shown in FIGS. 1 and 2, opposite ends 52 and 54 of the cylindrical surface 51 may be disposed between the members 14 and 16 of the transverse tension strength measuring apparatus 10. The parallel planar plies 50 and the parallel fibers 53 may be disposed parallel to direction 44 of a compression-load 56 to be applied to the composite specimen 18 by member 14 towards member 16. In other embodiments, the parallel planar plies 50 may be disposed parallel to direction 44 of the compression-load 56, but the fibers 53 within the parallel planar plies 50 may be disposed non-parallel to direction 44 of the compression-load 56. The composite specimen 18 does not have or require a grip for gripping the composite specimen 18. The composite specimen 18 may comprise a composite material, a brittle material, a material of a nozzle, a material of a rocket nozzle, a material of an aircraft device, and/or another type of material.

Member 14 may be used for applying the compression load 56 to the composite specimen 18 to compress the composite specimen 18 between members 14 and 16. Member 14 may be in contact with the test machine 22 through the bearing 20, which may comprise a ball bearing, disposed between member 14 and the test machine 22. The test machine 22 may move member 14 in the direction 44 against the composite specimen 18. By applying the compression load 56 to the cylindrical surface 51 of the composite specimen 18 in direction 44, a failure 58 of the composite specimen 18 may be created due to a transverse tensile stress 60 in the composite specimen 18 occurring transverse to the plies 50. The failure 58 may comprise a crack and/or irregularity in the composite specimen 18. The transverse tension strength 62 of the composite specimen 18 transverse to the plies 50 may be determined by using the following equation: transverse tension strength 62= (2×compression load 56)/(π×diameter 46×thickness 48). In other embodiments, the transverse tension strength 62 of the composite specimen 18 may be determined in various ways.

The temperature-changing device 26 may be adapted to change a temperature 25 of the composite specimen 18. The temperature-changing device 26 may comprise one or more lamps 26a, such as Quartz heating lamps, for heating the composite specimen 18. The temperature-changing device 26 may comprise a cooling chamber 26b for cooling the composite specimen. In other embodiments, the temperature-changing device 26 may vary. The temperature-measuring device 24 may be adapted to measure a temperature 25 of the composite specimen 18. The temperature-measuring device 24 may comprise a thermocouple comprising a thermocouple wire attached to the composite specimen 18. In other embodiments, the temperature-measuring device 24 may vary. The temperature-measuring device 24 may be inserted through the aperture 29 of the composite specimen 18. By using the temperature-changing device 26 to raise and lower the temperature 25 of the composite specimen 18 during application of the compression load 56 to the composite specimen 18, and by using the temperature-measuring device 24 to measure the temperature of the composite specimen 18 at failure 58, the transverse tension strength 62 of the composite specimen 18 may be determined at a range 31 of temperatures 25.

The range 31 may comprise elevated temperatures 25 between 100° F. up to approximately 2,500° F. if the tension strength measuring apparatus 10 is made from high strength steel, and up to approximately 5,000° F. if the tension strength measuring apparatus 10 is made from material capable of withstanding the test temperature. For example, for ultrahigh test temperatures, materials such as graphite or various metal-carbides may be used for fabricating the tension strength measuring apparatus 10. An alternate method for performing the tests at high temperatures which are greater than 2,500° F. is to insulate the tension strength measuring apparatus 10 with appropriate material. To measure the transverse tension strength at cryogenic temperatures in the range of 0° F. to −400° F., the tension strength measuring apparatus 10 shown in FIG. 1 may need to be placed in the cooling chamber 26b. In still other embodiments, the range 31 may comprise ambient temperatures 25.

Figure 6:
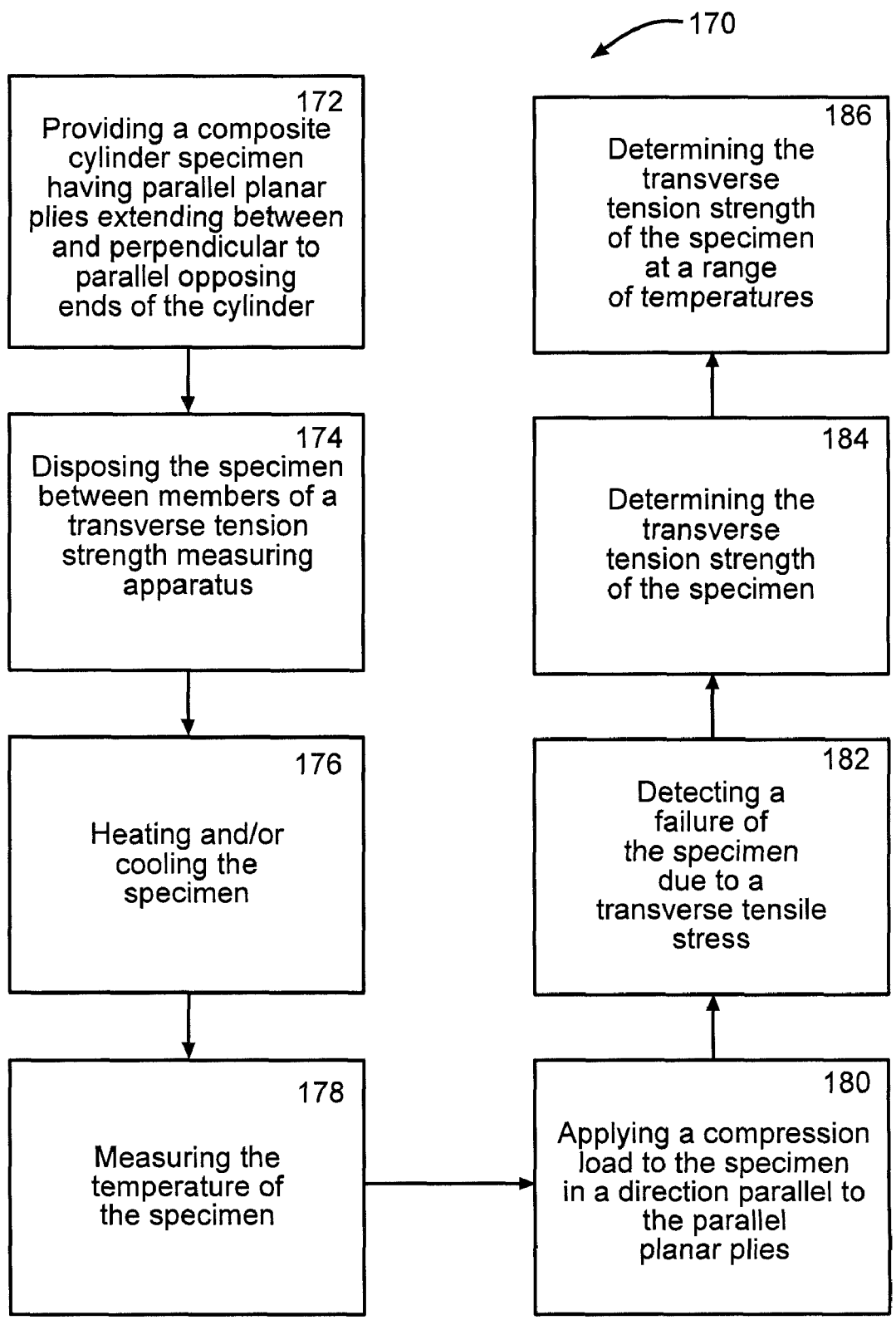
FIG. 6 illustrates a flowchart of one embodiment of a method for measuring a transverse tension strength of a composite specimen.

FIG. 6 illustrates a flowchart of one embodiment of a method 170 for measuring a transverse tension strength 62 of a composite specimen 18. In step 172, a composite specimen 18 may be provided comprising a solid cylinder, such as a disc or short cylinder, having parallel opposing ends 45 and 47 and a cylindrical surface 51 extending between and around the parallel opposing ends 45 and 47. Only parallel planar plies 50 may extend between and perpendicular to the parallel opposing ends 45 and 47. In one embodiment, the parallel planar plies 50 may comprise only parallel fibers 53 extending within the parallel planar plies 50 parallel to the parallel opposing ends 45 and 47. In other embodiments, the parallel planar plies 50 may comprise fibers 53 extending in varying parallel or non-parallel orientations within the parallel planar plies 50. The composite specimen 18 may comprise a diameter 46 of the parallel opposing ends 45 and 47, and a thickness 48 comprising a distance between the parallel opposing ends 45 and 47. The thickness 48 may be substantially shorter than the diameter 46 so that the composite specimen 18 forms a disc or a short cylinder to allow a uniform temperature of the composite specimen 18. In one embodiment, the thickness 48 may comprise at least one-quarter of the diameter 46. It may be important that the composite specimen 18 comprise a thickness 48 which is not too much larger than one-quarter of the diameter 46 because it may be difficult to obtain a uniform temperature throughout the composite specimen 18 if the thickness 48 is too large. Conversely, it may be important that the thickness 48 is not too much smaller than one-quarter of the diameter 46 to prevent the composite specimen 18 from buckling upon application of a compressive load. In other embodiments, the thickness 48 and diameter 46 may vary. The cylindrical surface 51 may be defined by an aperture 29. The composite specimen 18 may comprise any of the embodiments disclosed herein. In other embodiments, the composite specimen 18 may vary.

In step 174, opposite ends 52 and 54 of the cylindrical surface 51 of the composite specimen 18 may be disposed between members 14 and 16 of a transverse tension strength measuring apparatus 10. The parallel planar plies 50 and the parallel fibers 53 may be disposed perpendicular to members 14 and 16. In other embodiments, the parallel planar plies 50 may be disposed perpendicular to members 14 and 16, but the fibers 53 within the parallel planar plies 50 may be disposed non-perpendicular to member 14 and 16. Any of the embodiments of the transverse tension strength measuring apparatus 10 disclosed herein may be utilized, including any of the components of the apparatus 10. In other embodiments, the apparatus 10 may vary. Member 14 may comprise at least one of a load-applying member and a loading pin, and member 16 may comprise at least one of a support member and a stationary plate. In other embodiments, members 14 and 16 may vary. The parallel planar plies 50 and the parallel fibers 53 of the composite specimen 18 may be disposed to extend parallel to direction 44 between members 14 and 16. In other embodiments, the parallel planar plies 50 may be disposed to extend parallel to direction 44, but the fibers 53 within the parallel planar plies 50 may extend non-parallel to direction 44. In still other embodiments, the composite specimen 18 may be disposed in varying orientations.

In step 176, the composite specimen 18 may be heated and/or cooled. In one embodiment, step 176 may comprise using a temperature-changing device 26 to heat and/or cool the composite specimen 18. The temperature-changing device 26 may comprise one or more lamps 26a, such as Quartz heating lamps, for heating the composite specimen 18 and/or a cooling chamber 26b for cooling the composite specimen 18. In other embodiments, the temperature-changing device 26 may vary.

In step 178, the temperature 25 of the composite specimen 18 may be measured. In one embodiment, step 178 may comprise using a temperature-measuring device 24 to measure the temperature 25 of the composite specimen 18. The temperature 25 of the composite specimen 18 may be measured during heating and/or cooling of the specimen 18. The temperature-measuring device 24 may comprise a thermocouple comprising a thermocouple wire inserted through aperture 29 into the composite specimen 18. In other embodiments, the temperature-measuring device 24 may vary. The thermocouple may be attached to the aperture 29 of the composite specimen 18. In other embodiments, the temperature-measuring device 24 may be attached to the composite specimen 18 in various ways.

In step 180, a compression load 56 may be applied to the cylindrical surface 51 of the composite specimen 18 in the direction 44, parallel to the parallel planar plies 50 and the parallel fibers 53, using members 14 and 16 of the transverse tension strength measuring apparatus 10. In one embodiment, the compression load 56 may be applied parallel to the parallel planar plies 50, but non-parallel to the fibers 53 within the parallel planar plies 50. Step 180 may comprise moving member 14 using a test machine 22 towards member 16 to compress the composite specimen 18 in the direction 44 between member 14 and member 16.

In step 182, a failure 58 of the composite specimen 18 may be detected due to a transverse tensile stress 60 in the composite specimen 18 occurring transverse to the parallel planar plies 50 as a result of the compression load 56. In one embodiment, step 182 may comprise detecting a failure 58 comprising a crack and/or irregularity forming in the composite specimen 18.

In step 184, the transverse tension strength 62 of the composite specimen 18 transverse to the parallel planar plies 50 may be determined. In one embodiment, step 184 may comprise determining the transverse tension strength 62 of the composite specimen 18 using the following equation: transverse tension strength $62 = (2 \times \text{compression load } 56)/(\pi \times \text{diameter } 46 \text{ of the parallel opposing ends } 45 \text{ and } 47 \times \text{thickness } 48 \text{ comprising a distance between the parallel opposing ends } 45 \text{ and } 47)$. In other embodiments, the transverse tension strength 62 of the composite specimen 18 may be determined in various ways.

In step 186, the transverse tension strength 62 of the composite specimen 18 transverse to the parallel planar plies 50 may be determined at a range 31 of temperatures 25. The range 31 may comprise elevated temperatures 25 between 100° F. and 5,000° F., cryogenic temperatures 25 between 0° F. and −400° F., and/or ambient temperatures 25. In other embodiments, the range 31 of temperatures 25 may vary.

One or more embodiments of the disclosure may reduce and/or eliminate one or more problems experienced by one or more of the conventional apparatus and/or methods for measuring the transverse tension strength of a composite specimen. For instance, by using an apparatus having a composite specimen without a grip, the cost, time, and complexity of the apparatus and the testing may be decreased, especially at cryogenic and elevated temperatures. It has been estimated that one or more embodiments the disclosure may save up to 80 percent cost savings over one or more of the conventional apparatus and/or methods. Moreover, it has been verified that the embodiments disclosed yield accurate testing results. Further, other types of problems of one or more other conventional apparatus and/or methods may be reduced and/or eliminated.

It should be understood, of course, that the foregoing relates to exemplary embodiments of the disclosure and that modifications may be made without departing from the spirit and scope of the disclosure as set forth in the following claims.

I claim:

1. A composite specimen for conducting transverse tension strength testing comprising:
   a solid cylinder comprising parallel opposing ends, a cylindrical surface extending between and around the parallel opposing ends, and only parallel planar plies extending between the parallel opposing ends, the parallel planar plies comprising fibers extending within the parallel planar plies.

2. The composite specimen of claim 1 wherein the solid cylinder comprises a diameter of the parallel opposing ends and a thickness comprising a distance between the parallel opposing ends, wherein the thickness is at least one-quarter of the diameter.

3. The composite specimen of claim 2 wherein the thickness is substantially one-quarter of the diameter.

4. The composite specimen of claim 1 wherein the solid cylinder comprises an aperture for connecting a temperature-measuring device.

5. The composite specimen of claim 4 wherein the aperture is disposed in the cylindrical surface.

6. The composite specimen of claim 1 wherein the composite specimen is for disposing opposite ends of the cylindrical surface between members of a transverse tension strength measuring apparatus with the parallel planar plies disposed parallel to a direction of a compression-load to be applied to the composite specimen by the members.

7. The composite specimen of claim 1 wherein the composite specimen does not have a grip surface extending from the solid cylinder for gripping the composite specimen.

8. The composite specimen of claim 1 wherein the only parallel planar plies extend perpendicularly to the parallel opposing ends.

9. A transverse tension strength measuring apparatus comprising:
 a load-applying member for applying a compression load;
 a support member disposed in alignment with the load-applying member; and
 a composite specimen comprising a solid cylinder comprising parallel opposing ends, a cylindrical surface extending between and around the parallel opposing ends, and only parallel planar plies extending between the parallel opposing ends, the parallel planar plies comprising fibers extending within the parallel planar plies;
 wherein opposite ends of the cylindrical surface of the composite specimen are oriented between the support member and the load-applying member so that the load-applying member will apply the compression load to the cylindrical surface in a direction parallel to the parallel planar plies.

10. The transverse tension strength measuring apparatus of claim 9 wherein the load-applying member comprises a loading pin and the support member comprises a plate.

11. The transverse tension strength measuring apparatus of claim 9 further comprising at least one of a temperature-measuring device and a thermocouple attached to the composite specimen for measuring a temperature of the composite specimen.

12. The transverse tension strength measuring apparatus of claim 9 further comprising a temperature-changing device for at least one of heating and cooling the composite specimen.

13. The transverse tension strength measuring apparatus of claim 12 wherein the temperature-changing device comprises at least one of a lamp for heating the composite specimen and a chamber for cooling the composite specimen.

14. The transverse tension strength measuring apparatus of claim 9 wherein the solid cylinder comprises a diameter of the parallel opposing ends and a thickness comprising a distance between the parallel opposing ends, wherein the thickness is at least one-quarter of the diameter.

15. The transverse tension strength measuring apparatus of claim 14 wherein the thickness is substantially one-quarter of the diameter.

16. The transverse tension strength measuring apparatus of claim 9 further comprising a housing having a top surface, a bottom surface, and side surfaces, wherein the top surface is defined by a hole extending from the top surface towards the bottom surface, and at least one of the side surfaces is defined by a cavity extending from the at least one side surface towards another side surface, wherein the hole and the cavity intersect within the housing.

17. The transverse tension strength measuring apparatus of claim 16 wherein the load-applying member is moveably disposed in the hole, and the support member is disposed within the cavity in alignment with the load-applying member.

18. The transverse tension strength measuring apparatus of claim 9 wherein the composite specimen does not have a grip surface extending from the solid cylinder for the transverse tension strength measuring apparatus to grip the composite specimen.

19. The transverse tension strength measuring apparatus of claim 9 wherein the only parallel planar plies extend perpendicularly to the parallel opposing ends.

20. A method for measuring a transverse tension strength of a composite specimen comprising:
 providing a composite specimen comprising a solid cylinder comprising parallel opposing ends, a cylindrical surface extending between and around the parallel opposing ends, and only parallel planar plies extending between the parallel opposing ends, the parallel planar plies comprising fibers extending within the parallel planar plies;
 disposing opposite ends of the cylindrical surface of the composite specimen between members of a transverse tension strength measuring apparatus;
 applying a compression load to the cylindrical surface of the composite specimen in a direction parallel to the parallel planar plies using the members of the transverse tension strength measuring apparatus;
 detecting a failure of the composite specimen due a transverse tensile stress in the composite specimen occurring transverse to the parallel planar plies; and
 determining the transverse tension strength of the composite specimen.

21. The method of claim 20 wherein the solid cylinder comprises a diameter of the parallel opposing ends and a thickness comprising a distance between the parallel opposing ends, wherein the thickness is at least one-quarter of the diameter.

22. The method of claim 21 wherein the thickness is substantially one-quarter of the diameter.

23. The method of claim 20 wherein the disposing step comprises disposing the opposite ends of the cylindrical surface between the members of the transverse tension strength measuring apparatus with the parallel planar plies disposed perpendicularly to the members.

24. The method of claim 20 wherein the disposing step comprises disposing the opposite ends of the cylindrical surface between a load-applying member and a support member of the transverse tension strength measuring apparatus, and the applying step comprises applying the compression load to the cylindrical surface in a direction parallel to the parallel planar plies by moving the load-applying member towards the support member using the transverse tension strength measuring apparatus.

25. The method of claim 24 wherein the load-applying member comprises a loading pin and the support member comprises a stationary plate.

26. The method of claim 20 wherein the detecting step comprises detecting a crack forming in the composite specimen.

27. The method of claim 20 wherein the determining step comprises determining the transverse tension strength by using the following equation: transverse tension strength=(2×the compression load)/($\pi$×a diameter of the parallel opposing ends×a thickness comprising a distance between the parallel opposing ends).

28. The method of claim 20 further comprising the step of at least one of heating and cooling the composite specimen.

29. The method of claim 28 further comprising the step of measuring a temperature of the composite specimen during the at least one of heating and cooling of the composite specimen.

30. The method of claim 29 wherein at least one of the composite specimen is heated using a heating lamp, the composite specimen is cooled using a chamber, and the temperature of the composite specimen is measured using a thermocouple attached to the composite specimen.

31. The method of claim 29 further comprising the step of determining the transverse tension strength of the composite specimen at a range of temperatures, wherein the range comprises at least one of elevated temperatures between 100° F. and 5,000° F., and cryogenic temperatures between 0° F. and −400° F.

32. The method of claim 20 wherein the provided composite specimen does not have a grip surface extending from the solid cylinder for the transverse tension strength measuring apparatus to grip the composite specimen.

33. The method of claim 20 wherein the only parallel planar plies of the provided composite specimen extend perpendicularly to the parallel opposing ends.

* * * * *